United States Patent [19]

Maekawa et al.

[11] Patent Number: 5,241,117
[45] Date of Patent: Aug. 31, 1993

[54] PROCESS FOR PRODUCING SEMICARBAZIDE

[75] Inventors: Tsukasa Maekawa, Komatsujima; Hiroyasu Hayashi, Itano; Kazusaki Kamiya, Tokushima, all of Japan

[73] Assignee: Otsuka Kagaku Kabushiki Kaisha, Osaka, Japan

[21] Appl. No.: 920,289

[22] PCT Filed: Jun. 13, 1991

[86] PCT No.: PCT/JP91/00799
§ 371 Date: Aug. 3, 1992
§ 102(e) Date: Aug. 3, 1992

[87] PCT Pub. No.: WO92/12124
PCT Pub. Date: Jul. 23, 1992

[30] Foreign Application Priority Data

Dec. 27, 1990 [JP] Japan .................. 2-418849

[51] Int. Cl.$^5$ ............................. C07C 281/06
[52] U.S. Cl. ........................ 564/37; 564/34
[58] Field of Search .................. 564/34, 37

[56] References Cited

U.S. PATENT DOCUMENTS 4,482,738 11/1984 Rothgery .................. 564/37
4,725,608 2/1988 Nakaguchi et al. .......... 564/37 X Primary Examiner—Richard L. Raymond
Attorney, Agent, or Firm—Armstrong, Westerman, Hattori, McLeland & Naughton

[57] ABSTRACT

This invention provides a process for preparing semicarbazide comprising reacting the compound of the formula (I)

$$NH_2-C=N-Cl \quad (I)$$
$$\phantom{NH_2-C=}|$$
$$\phantom{NH_2-C=}O-Na$$

with ammonia in the absence or presence of chloride, hydroxide, sulfate, carbonate, acetate, salicylate, ammine complex or ethylenediamine complex of zinc or of cadmium, or a mixture thereof as catalyst. This process has the advantage of being free of the use of sodium hydroxide in large amounts or formation of byproduct sodium carbonate.

19 Claims, No Drawings

PROCESS FOR PRODUCING SEMICARBAZIDE

TECHNICAL FIELD

The present invention relates to a novel process for producing semicarbazide.

Semicarbazide is a compound useful as a raw material for agrochemicals, medicinals and photographic chemicals, as a reagent for identifying aldehydes and ketones and, in particular, as a raw material for the blowing agent azodicarbonamide.

BACKGROUND ART

A process known for the production of semicarbazide uses hydrazine and urea as starting materials. Another known process starts from hydrazine and a cyanate.

Since the raw material hydrazine is expensive, these processes give semicarbazide at high cost, hence are disadvantageous.

Hydrazine is produced by oxidation of ammonia. More specifically, the Raschig, organic, and hydrogen peroxide processes may be mentioned, among others. In any process, however, energy and cost are required for concentration from a dilute solution and for ketazine hydrolysis, for instance, inevitably rendering the product hydrazine expensive.

Hydrazine can also be produced by oxidation of urea. This process is known as the urea process, and the production route to semicarbazide from the thus-obtained hydrazine is as follows:

$$NH_2CONH_2 + 4NaOH + Cl_2 \rightarrow N_2H_4 \cdot H_2O + Na_2CO_3 + 2NaCl + H_2O \quad (1)$$

$$N_2H_4 \cdot H_2O + NH_2CONH_2 \rightarrow NH_2CONHNH_2 + NH_3 + H_2O \quad (2)$$

The above equations (1) and (2) give the following equation (3):

$$2NH_2CONH_2 + 4NaOH + Cl_2 \rightarrow NH_2CONHNH_2 + Na_2CO_3 + 2NaCl + NH_3 + 2H_2O \quad (3)$$

The urea process requires sodium hydroxide in large amounts for the production of hydrazine and allows formation of the byproduct sodium carbonate, which requires cost of treatment. Consequently, the hydrazine production cost becomes high.

For producing semicarbazide using the abovementioned urea process, sodium hydroxide and urea are required in large amounts and costs are needed also for the treatment of the byproducts sodium carbonate and ammonia. As a result, the hydrazine production still costs high.

DISCLOSURE OF THE INVENTION

Accordingly, it is an object of the present invention to provide an economically advantageous process for producing semicarbazide which can avoid the use of sodium hydroxide in large quantities, the formation of the byproduct sodium carbonate and the costs of treatment thereof.

Intensive investigations made by the present inventors in an attempt to radically remove the drawbacks of the prior art processes mentioned above have now led to a novel process for producing semicarbazide economically in good yields.

Thus the present invention provides a process for producing semicarbazide which comprises reacting the compound represented by the formula (I)

with ammonia.

The invention further provides a process for producing semicarbazide which comprises reacting the compound represented by the formula (I) with ammonia in the presence of a chloride, hydroxide, sulfate, carbonate, acetate, salicylate, ammine complex or ethylenediamine complex of zinc or of cadmium, or a mixture of these acting as catalyst.

As distinguished from the prior art processes, the novel process according to the invention does not use hydrazine as a starting material but gives semicarbazide from the compound of the formula (I) and ammonia.

In the present invention, a compound of the formula (I)

is used as one of the starting materials. This compound represented by the formula (I) is known per se as described in "Hydrazine—properties and application thereof" authored by Toshio YOKOTA and published by Chijin Shokan on Mar. 10, 1968, page 9, and can be named monochlorourea sodium salt. Hereinafter, the compound of the above formula (I) will be referred to as "monochlorourea sodium salt" in this specification. With respect to monochlorourea sodium salt of the formula (I), the following resonance can be mentioned, and said compound can be represented by the formula (II)

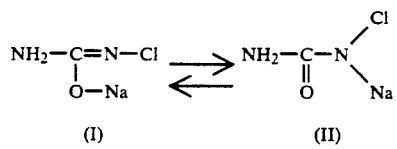

Monochlorourea sodium salt represented by the formula (I) can be prepared in the conventional manner without any particular limitation, for example by the following process:

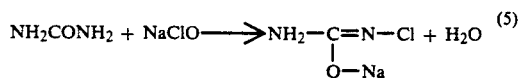

As illustrated above, monochlorourea sodium salt of the formula (I) is generally prepared using urea, sodium hydroxide and chlorine as raw materials.

Thus, in other words, the process of the invention is a novel process that produces semicarbazide from monochlorourea sodium salt prepared from urea, sodium hydroxide and chlorine, and ammonia.

When expressed in terms of the raw materials mentioned above, the production route to semicarbazide according to the invention may be defined as follows:

$$NH_2CONH_2 + 2NaOH + Cl_2 + NH_3 \rightarrow NH_2CONHNH_2 + 2NaCl + 2H_2O \quad (6)$$

In the semicarbazide production according to the invention, sodium hydroxide and urea are required only in small amounts and no byproduct sodium carbonate is formed. The process of the invention is rational in these respects.

Comparison between the process of the present invention and the urea process as specifiable by the equations (6) and (3), respectively, reveals that the process of the invention is very economical in that, in the process of the invention, the amounts of urea and sodium hydroxide can each be reduced to half.

As can be understood from the foregoing, the novel process of the invention is rational from the reaction viewpoint and can give semicarbazide economically at low cost. Furthermore, when this semicarbazide is used, it is possible to produce azodicarbonamide rationally and at low cost.

As for the reaction mechanisms, investigations with the radioisotope $N^{15}$-containing compound have revealed that the following reactions are involved in the process of the invention:

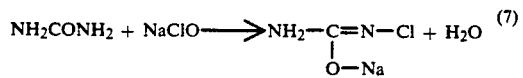

(7)

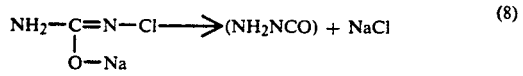

(8)

(NH$_2$NCO) + NH$_3$ ⟶ NH$_2$NHCONH$_2$   (9)

Thus, monochlorourea sodium salt of the formula (I) undergoes rearrangement to give amino isocyanate. Probably due to its high reactivity, this amino isocyanate as such cannot be isolated but reacts with ammonia to give semicarbazide. Mass spectrometry of the semicarbazide synthesized from the $N^{15}$ compound and the semicarbazide synthesized from the ordinary $N^{14}$ compound has revealed the involvement of the above reactions (7)-(9).

Thus, the process of the invention, as indicated by the above reaction equations (7)-(9), involves rearrangement of monochlorourea sodium salt to amino isocyanate and addition of ammonia to this amino isocyanate for the formation of semicarbazide. This is a novel finding that has been hithertofore unknown, and led to the novel process for preparing semicarbazide. The process of the invention does not involve the formation of semicarbazide by the reaction of hydrazine formed in the urea process route with the remaining urea. It is to be noted, however, that the above description of reaction mechanisms is by no means limitative of the scope of the present invention.

Generally speaking, the reaction system in the process of the invention contains sodium hydroxide, water and ammonia as active hydrogen-containing compounds. If amino isocyanate should react with sodium hydroxide, hydrazine would be formed via sodium carbazate. However, the amount of sodium hydroxide is small and the hydrazine formation is little. As for the reactivity for water and for ammonia, amino isocyanate seems to react with ammonia at a higher reaction rate than with water. Therefore, in the process of the present invention, semicarbazide is formed almost selectively and in high yields.

Embodiments of the process of the invention is now described in further detail. The description, however, is by no means limitative of the scope of the invention.

The preparation of monochlorourea sodium salt of the formula (I) is first described, which particularly comprises the step of synthesizing sodium hypochlorite or monochlorourea and the subsequent step of synthesizing monochlorourea sodium salt, and then the step of synthesizing semicarbazide is described.

Sodium hypochlorite is synthesized in the conventional manner, namely by reacting sodium hydroxide aqueous solution with gaseous chlorine. In this step, it is important that sodium hydroxide should be used in slight excess, that the available chlorine should be 10 to 15%, and that the temperature should not be very high.

Monochlorourea can be produced also in the conventional manner. Thus, for instance, tert-butyl hypochlorite is added to a solution of urea in methanol for reaction, the reaction mixture is concentrated under reduced pressure, and the resulting crystals of monochlorourea are collected. The content of monochlorourea depends on the excess urea.

Monochlorourea sodium salt of the formula (I) is synthesized by adding an aqueous solution of sodium hypochlorite to an aqueous solution of urea at a temperature of 5° to 10° C. In this case, care should be taken not to increase the temperature too much. Per mole of sodium hypochlorite, urea is used in an amount of 1 mole theoretically, but should preferably be used in excess for example in an amount of about 1 to 2 moles, so as to avoid deficiency of urea. This reaction is illustrated by the following reaction equation.

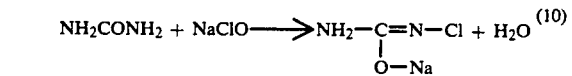

(10)

Monochlorourea sodium salt (I) can be synthesized also by adding crystalline monochlorourea or an aqueous solution of monochlorourea to an aqueous solution of sodium hydroxide. In this case, again, the temperature should not be too high and should preferably be maintained at about 5° to 10° C. Per mole of monochlorourea, sodium hydroxide is theoretically used in an amount of 1 mole, but should preferably be used in an amount of about 1 to 1.5 moles, so as to avoid deficiency of sodium hydroxide. This reaction is illustrated by the following reaction equation.

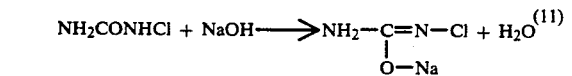

(11)

Furthermore, monochlorourea sodium salt of the formura (I) can also be synthesized by blowing chlorine gradually into a mixed aqueous solution containing urea and sodium hydroxide. In this case, again, the temperature should not be too high and should preferably be maintained at about 5° to 10° C., and urea and sodium hydroxide are used in theoretical amounts, i.e., 1 mole and 2 moles, respectively, and preferably in amounts of about 1 to 2 moles and 2 to 3 moles, respectively, per mole of chlorine, so as to avoid deficiency of urea and sodium hydroxide. This reaction is illustrated by the following reaction equation.

 (12)

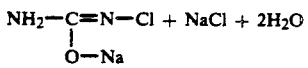

Some typical procedures for the preparation of monochlorourea sodium salt by the methods mentioned above will be described later herein.

Semicarbazide is prepared by reacting the thus obtained monochlorourea sodium salt and ammonia in the presence of water and/or ammonia acting as solvent. The reaction is preferably conducted in a solution state, but can proceed even if the reaction system is in the form of a slurry.

Semicarbazide is typically synthesized by adding aqueous ammonia or liquid ammonia to an aqueous solution of monochlorourea sodium salt of the formula (I) prepared in the above manner and allowing the reaction to proceed. The reaction should preferably be carried out in a closed system so that ammonia can be prevented from escaping from the reaction system, although open reaction systems also allow the formation of semicarbazide. The reaction may proceed even at a low temperature but, for acceleration, it should preferably be carried out at about 50° to 150° C. Although 1 mole of ammonia per mole of monochlorourea sodium salt is sufficient for semicarbazide formation, ammonia should preferably be used, for increasing the reactivity, in an amount of about 10 to 1,000 moles, more preferably about 50 to 500 moles, per mole of monochlorourea sodium salt. When the reaction is conducted in a closed system, the reaction system pressure may vary depending on the amount of ammonia and on the reaction temperature but generally amounts to about 10 to 100 kg/cm$^2$.

Ammonia should preferably be used in the form of liquid ammonia for increased concentration and increased reactivity purposes although aqueous ammonia may also be used. When ammonia is used in the form of aqueous ammonia, the ammonia concentration should preferably be about 10 to 28 percent by weight.

The process according to the invention can give semicarbazide in high yields even in the absence of any catalyst. For further improvements in reactivity and yield, however, the present inventors searched for a catalyst.

As a result, it has been found that the compounds mentioned below under (A) and (B) are effective as novel catalysts for the production of semicarbazide.
(A) Chloride, hydroxide, sulfate, carbonate, acetate, or salicylate of zinc or of cadmium;
(B) Ammine complex or ethylenediamine complex of zinc or of cadmium.

The mechanisms of action of these catalysts have not been clear as yet. The effects of the amount of ammonia and the presence or absence of such a catalyst on the yield are as follows. When the amount of ammonia is relatively small, the yield is markedly increased by the presence of the catalyst. The difference in yield between the presence of the catalyst and the absence thereof decreases as the amount of ammonia increases. Still, however, the yield is higher in the presence of the catalyst than in the absence thereof.

The catalyst amount is not critical. Generally, however, the catalysts mentioned above are used in an amount of up to 1 mole, preferably about 0.1 to 0.5 mole, per mole of monochlorourea sodium salt. The catalysts may be used either alone or in combination.

Substantially the same reaction conditions as mentioned above are applicable also to the cases where any of the above catalysts is used. Generally, the use of the catalyst tends to reduce the amount of ammonia to be used.

The process of the invention can be carried out either batchwise or continuously.

After completion of the reaction, the unreacted ammonia is recovered. The recovered ammonia can be recycled. The remainder after ammonia recovery is a semicarbazide solution. This solution as such may be used as a raw material for the production of hydrazodicarbonamide, or alternatively hydrochloric acid, for example, may be added to said solution for isolation of semicarbazide hydrochloride.

The semicarbazide thus obtained can be converted into azodicarbonamide via hydrazodicarbonamide.

Hydrazodicarbonamide is synthesized by reacting the aqueous semicarbazide solution as obtained in the above manner after ammonia recovery, or a solution of semicarbazide hydrochloride in water or the like, with about 1 to 1.2 moles, per mole of semicarbazide, of urea. Generally, the reaction is carried out preferably at a pH of 7 or below as adjusted to by addition of an acid, such as sulfuric acid or hydrochloric acid, and at a temperature of about 90° to 105° C., although the reaction is not limited thereto and may also be carried out at a higher pH.

Azodicarbonamide is synthesized in the conventional manner. Thus, the above hydrazodicarbonamide, either in the reaction mixture form or in the form of crystals isolated, is oxidized in an aqueous medium with an oxidizing agent, such as chlorine or hydrogen peroxide, at a temperature of about 10° to 50° C. The oxidizing agent is preferably used in an amount of about 1 to 1.2 moles per mole of hydrazodicarbonamide.

EXAMPLES

The following examples are further illustrative of the present invention but are by no means limitative of the scope thereof.

For simicarbazide production, monochlorourea sodium salt was prepared by the following procedures, for instance.

(A) A 200-ml four-necked flask equipped with a thermometer and a stirrer was charged with 9 g (0.15 mole) of urea and 30 g of water, and the contents were cooled to 5° C. with stirring. To this solution was added dropwise 63.08 g (0.1 mole) of a sodium hypochlorite aqueous solution with an available chlorine of 11.26% by weight over 30 minutes with cooling at 5° to 10 ° C.

After completion of the dropwise addition, the monochlorourea sodium salt solution obtained was analyzed by iodometry and high-performance liquid chromatography. The available chlorine was thus found to be 6.89% by weight. This corresponded to a yield of 99% (mole percent; hereinafter the same shall apply).

(B) A 200-ml four-necked flask equipped with a thermometer and a stirrer was charged with 90 g of a sodium hydroxide solution (concentration: 5.56% by weight), and the solution was cooled to 5° C. with stirring.

To this solution was added portionwise 10.05 g (0.1 mole) of crystalline monochlorourea with an available chlorine of 70.65% by weight as prepared in advance by the known method (e.g. Journal of the American Chemical Society, 76, 2572 (1954).

After completion of the addition, the monochlorourea sodium salt solution obtained wa analyzed by iodometry and high-performance liquid chromatography, whereby the available chlorine was found to be 7.03% by weight. This corresponded to a yield of 99%.

(B') A 200-ml four-necked flask equipped with a thermometer and a stirrer was cooled to −30° C. and charged with 221 g (13 moles) of liquid ammonia. Subsequently 5 g (0.125 mole) of sodium hydroxide was added thereto, and to the resulting mixture was added portionwise 10.05 g (0.1 mole) of crystals of monochlorourea with an available chlorine of 70.65% by weight as prepared beforehand by the known method (e.g. Journal of the American Chemical Society, 76, 2572 (1954)).

After completion of the addition, the monochlorourea sodium salt solution obtained was analyzed by iodometry and high-performance liquid chromatography, whereby the available chlorine was found to be 2.98% by weight. This corresponded to a yield of 99%.

(C) A 200-ml four-necked flask equipped with a thermometer and a stirrer was charged with 100.4 g of 11.35 weight percent aqueous solution of urea, which contained 5 g of sodium hydroxide, and the solution was cooled to 5° C. with stirring.

Chlorine gas was introduced into the above solution until absorption of 7.1 g (0.1 mole) of chlorine. Thereafter, the monochlorourea sodium salt solution obtained was analyzed by iodometry and high-performance liquid chromatography, whereby the available chlorine was found to be 6.54% by weight. This corresponds to a yield of 99%.

EXAMPLE 1

A 300-ml stainless steel autoclave equipped with a stirrer, a thermometer and a pressure gauge was charged with 51.62 g (0.05 mole) of the monochlorourea sodium salt solution (available chlorine 6.89% by weight) obtained by the above procedure (A) with cooling to 5° to 10°C.

Then, the autoclave was charged with 85 g (5 moles) of liquid ammonia with stirring and then charged with 20.4 g (0.015 mole) of 10 weight percent aqueous solution of zinc chloride, and the contents were heated at 70° C. using a mantle heater. Under these conditions the pressure of the reaction system was indicated to be 25 kg/cm². After 30 minutes of heating, the autoclave was cooled, the unreacted ammonia was purged off, and the reaction product containing reducing substances such as semicarbazide, hydrazine and the like was obtained. Oxidation-reduction titration indicated that the yield of said reducing substances was 96%. Liquid chromatographic analysis indicated that the yield of semicarbazide was 3.38 g or 90%.

This reaction mixture was concentrated and then acidified by addition of concentrated hydrochloric acid. The resultant crystals were collected by filtration and recrystallized from a solvent mixture composed of ethanol and water to give white crystals. These crystals were subjected to IR, NMR and mass spectrometry. The spectral data obtained were in complete agreement with those obtained with an authentic sample of semicarbazide hydrochloride synthesized separately. Thus the crystals were identified as semicarbazide hydrochloride.

The same analytical procedure as used in this example was followed also in yield determination in Example 2 and the subsequent examples.

EXAMPLES 2 TO 7

The procedure of Example 1 was followed using the zinc salt or cadmium salt specified below in Table 1 as the catalyst in lieu of zinc chloride ($ZnCl_2$).

The yield of reducing substances and of semicarbazide thus attained are also shown in Table 1.

TABLE 1

| Example | Catalyst | Yield (%) Semicarbazide | Reducing substances |
|---|---|---|---|
| 2 | $ZnSO_4 \cdot 7H_2O$ | 90 | 95 |
| 3 | $Zn(OH)_2$ | 91 | 96 |
| 4 | $ZnCO_3$ | 90 | 95 |
| 5 | $Zn(CH_3CO_2)_2 \cdot 2H_2O$ | 89 | 94 |
| 6 | $Zn[C_6H_4(OH)CO_2]_2 \cdot 3H_2O$ | 89 | 94 |
| 7 | $CdCl_2$ | 88 | 93 |

EXAMPLES 8 AND 9

The procedure of Example 1 was followed using ammine complex of zinc or cadmium as the catalyst in lieu of zinc chloride.

The ammine complex of zinc or cadmium was prepared, for example, in the following manner.

Preparation of Ammine Complex

Zinc chloride (0.68 g, 0.005 mole) was added portionwise to 18.36 g of 25 weight percent aqueous ammonia at 5° C., whereby a completely homogeneous solution was obtained.

The reaction was conducted in the same manner as in Example 1 except that the complex (0.005 mole) prepared in the above manner was used.

The yield of reducing substances and of semicarbazide are shown in Table 2.

TABLE 2

| Example | Catalyst | Yield (%) Semicarbazide | Reducing substances |
|---|---|---|---|
| 8 | Zinc-ammine complex | 90 | 95 |
| 9 | Cadmium-ammine complex | 89 | 93 |

EXAMPLE 10

The procedure of Example 1 was followed using ethylenediamine complex of zinc as the catalyst in lieu of zinc chloride. The ethylenediamine complex was prepared, for example, in the following manner.

Preparation of Ethylenediamine Complex

Zinc chloride (1.02 g, 0.0075 mole) was dissolved portionwise in 18.36 g of 25 weight percent aqueous ammonia at 5° C., followed by addition of 0.45 g (0.0075 mole) of ethylenediamine.

Using the complex (0.0075 mole) prepared in the above manner, the procedure of Example 1 was followed. Reducing substances were obtained in a yield of 93%. The yield of semicarbazide was 88%.

EXAMPLES 11 AND 12

The procedure of Example 1 was followed using, as the catalyst, a zinc salt (0.0075 mole) and a candmium salt (0.0075 mole) combinedly as shown in Table 3 below. The yields of reducing substances and of semicarbazide are shown in Table 3.

TABLE 3

| | | Yield (%) | |
|---|---|---|---|
| Example | Catalyst | Semicarbazide | Reducing substances |
| 11 | $ZnCl_2 + CdCl_2$ | 87 | 92 |
| 12 | $ZnSO_4 \cdot 7H_2O + CdCl_2$ | 87 | 92 |

EXAMPLE 13

The reaction was carried out under the same conditions as used in Example 1 except that no catalyst was used. Reducing substances were obtained in a yield of 78% as determined by oxidation-reduction titration. The semicarbazide yield was 72%.

EXAMPLES 14 TO 16

The reaction was carried out under the same conditions as used in Example 1 except that the amount of liquid ammonia relative to the compound of the formula (I) was varied as shown below in Table 4. The yield data are also shown in Table 4.

TABLE 4

| | Amount of ammonia | Yield (%) | |
|---|---|---|---|
| Example | $NH_3$/compound (I) (mole ratio) | Semi-carbazide | Reducing substances |
| 14 | 10 | 71 | 77 |
| 15 | 50 | 84 | 88 |
| 16 | 500 | 95 | 96 |

EXAMPLES 17 TO 19

The reaction was carried out under the same conditions as used in Examples 14 to 16 except that no catalyst was used. The yields of reducing substances and of semicarbazide are shown in Table 5.

TABLE 5

| | Amount of ammonia | Yield (%) | |
|---|---|---|---|
| Example | $NH_3$/compound (I) (mole ratio) | Semi-carbazide | Reducing substances |
| 17 | 10 | 51 | 55 |
| 18 | 50 | 60 | 65 |
| 19 | 500 | 90 | 92 |

EXAMPLE 20

A 300-ml stainless steel autoclave equipped with a stirrer, a thermometer and a pressure gauge was charged with 236.05 g (0.1 mole) of monochlorourea sodium salt solution prepared in the procedure (B') mentioned above and then with 4.08 g (0.03 mole) of zinc chloride with stirring.

Subsequently, the autoclave was tightly closed and heated to 70° C. with stirring. The reaction was continued at that temperature for 30 minutes, and then the unreacted ammonia was purged off. Reducing substances were obtained in a yield of 73%. The yield of semicarbazide was 70%.

EXAMPLE 21

A 300-ml four-necked flask equipped with a stirrer and a thermometer was charged with 50.50 g (0.05 mole) of the monochlorourea sodium salt solution prepared by the procedure (B) mentioned above with cooling at 5° to 10° C.

Then, the flask was charged with 170 g (2.5 moles) of 25 weight percent aqueous ammonia and finally with 20.4 g (0.015 mole) of 10 weight percent aqueous solution of zinc chloride. Stirring was then continued at 25° C. for 3 hours.

The unreacted ammonia was purged off from the reaction mixture. The yield of reducing substances was 76%. The semicarbazide yield was 70%.

EXAMPLES 22 TO 26

The reaction was carried out under the same conditions as used in Example 1 except that 54.28 g (0.05 mole) of the monochlorourea sodium salt solution (available chlorine 6.54% by weight) prepared by the procedure (C) mentioned above was used and that the reaction temperature and time were varied as shown below in Table 6. The yield data are also shown in Table 6.

TABLE 6

| | Reaction temperature (°C.) | Reaction time (min.) | Yield (%) | |
|---|---|---|---|---|
| Example | | | Semi-carbazide | Reducing substances |
| 22 | 25 | 180 | 81 | 84 |
| 23 | 50 | 60 | 85 | 90 |
| 24 | 100 | 30 | 91 | 96 |
| 25 | 120 | 30 | 89 | 94 |
| 26 | 150 | 30 | 85 | 90 |

We claim:

1. A process for producing semicarbazide which comprises reacting the compound of the formula (I)

with ammonia.

2. A process as claimed in claim 1, wherein ammonia is used in an amount of about 10 to 1,000 moles per mole of the compound of the formula (I).

3. A process as claimed in claim 1, wherein ammonia is used in an amount of about 50 to 500 moles per mole of the compound of the formula (I).

4. A process as claimed in claim 1, wherein ammonia is used in the form of liquid ammonia.

5. A process as claimed in claim 1, wherein ammonia is used in the form of aqueous ammonia.

6. A process as claimed in claim 1, wherein the reaction is carried out in a closed system.

7. A process as claimed in claim 1, wherein the reaction is carried out at a temperature of about 50° to 150° C.

8. A process as claimed in claim 1, wherein the compound of the formula (I) is reacted with ammonia in the presence of chloride, hydroxide, sulfate, carbonate, acetate, salicylate, ammine complex or ethylenediamine complex of zinc or of cadmium, or a mixture thereof as catalyst.

9. A process as claimed in claim 8, wherein the catalyst is used in an amount of up to 1 mole per mole of the compound of the formula (I).

10. A process as claimed in claim 8, wherein the catalyst is used in an amount of about 0.1 to 0.5 mole per mole of the compound of the formula (I).

11. A process as claimed in claim 8, wherein ammonia is used in an amount of about 10 to 1,000 moles per mole of the compound of the formula (I).

12. A process as claimed in claim 8, wherein ammonia is used in an amount of about 50 to 500 moles per mole of the compound of the formula (I).

13. A process as claimed in claim 8, wherein ammonia is used in the form of liquid ammonia.

14. A process as claimed in claim 8, wherein ammonia is used in the form of aqueous ammonia.

15. A process as claimed in claim 8, wherein the reaction is carried out in a closed system.

16. A process as claimed in claim 8, wherein the reaction is carried out at a temperature of about 50° to 150° C.

17. A process as claimed in claim 1, wherein the compound of the formula (I) is prepared by reacting urea and sodium hypochlorite.

18. A process as claimed in claim 1, wherein the compound of the formula (I) is prepared by reacting monochlorourea and sodium hydroxide.

19. A process as claimed in claim 1, wherein the compound of the formula (I) is prepared by reacting urea, sodium hydroxide and chlorine.

* * * * *

UNITED STATES PATENT AND TRADEMARK OFFICE
CERTIFICATE OF CORRECTION

PATENT NO. : 5,241,117

DATED : August 31, 1993

INVENTOR(S) : Maekawa et al

It is certified that error appears in the above-identified patent and that said Letters Patent is hereby corrected as shown below:

On the cover page, Item [86], PCT § 371 Date should be --Aug. 13, 1992-- and the § 102(e) Date should be --Aug. 13, 1992--.

Signed and Sealed this

Seventeenth Day of May, 1994

*Attest:*

BRUCE LEHMAN

*Attesting Officer*     *Commissioner of Patents and Trademarks*